(12) United States Patent
Mazin

(10) Patent No.: US 8,461,538 B2
(45) Date of Patent: Jun. 11, 2013

(54) METHOD AND APPARATUS FOR EMISSION GUIDED RADIATION THERAPY

(75) Inventor: Samuel Mazin, Menlo Park, CA (US)

(73) Assignee: RefleXion Medical, Inc., Burlingame, CA (US)

( * ) Notice: Subject to any disclaimer, the term of this patent is extended or adjusted under 35 U.S.C. 154(b) by 0 days.

(21) Appl. No.: 13/209,275

(22) Filed: Aug. 12, 2011

(65) Prior Publication Data

US 2011/0291015 A1 Dec. 1, 2011

Related U.S. Application Data

(63) Continuation of application No. 12/367,679, filed on Feb. 9, 2009, now Pat. No. 8,017,915.

(60) Provisional application No. 61/036,709, filed on Mar. 14, 2008.

(51) Int. Cl.
*A61N 5/10* (2006.01)

(52) U.S. Cl.
USPC ............... 250/363.04; 250/492.1; 250/492.3; 378/63; 378/65; 600/427

(58) Field of Classification Search
USPC .......................................................... 378/63
See application file for complete search history.

(56) References Cited

U.S. PATENT DOCUMENTS

| | | | |
|---|---|---|---|
| 5,813,985 A | 9/1998 | Carroll | |
| 6,735,277 B2 | 5/2004 | McNutt et al. | |
| 7,110,808 B2 | 9/2006 | Adair | |
| 7,199,382 B2 | 4/2007 | Rigney et al. | |
| 7,227,925 B1 | 6/2007 | Mansfield et al. | |
| 7,265,356 B2 | 9/2007 | Pelizzari et al. | |
| 7,280,633 B2 | 10/2007 | Cheng et al. | |
| 7,453,983 B2 | 11/2008 | Schildkraut et al. | |
| 7,983,380 B2 * | 7/2011 | Guertin et al. | 378/4 |
| 8,017,915 B2 | 9/2011 | Mazin | |
| 2002/0191734 A1* | 12/2002 | Kojima et al. | 378/4 |
| 2002/0193685 A1 | 12/2002 | Mate et al. | |
| 2003/0219098 A1 | 11/2003 | McNutt et al. | |
| 2004/0030246 A1* | 2/2004 | Townsend et al. | 600/427 |
| 2004/0057557 A1* | 3/2004 | Nafstadius | 378/209 |

(Continued)

FOREIGN PATENT DOCUMENTS

| | | |
|---|---|---|
| WO | WO-2007/124760 A1 | 11/2007 |
| WO | WO-2009/114117 A2 | 9/2009 |
| WO | WO-2012/135771 A1 | 10/2012 |

OTHER PUBLICATIONS

International Search Report mailed on Jul. 20, 2012, for PCT Patent Application No. PCT/US2012/031704, filed on Mar. 30, 2012, 3 pages.

(Continued)

*Primary Examiner* — David Porta
*Assistant Examiner* — Djura Malevic
(74) *Attorney, Agent, or Firm* — Morrison & Foerster LLP

(57) ABSTRACT

An apparatus comprising a radiation source, coincident positron emission detectors configured to detect coincident positron annihilation emissions originating within a coordinate system, and a controller coupled to the radiation source and the coincident positron emission detectors, the controller configured to identify coincident positron annihilation emission paths intersecting one or more volumes in the coordinate system and align the radiation source along an identified coincident positron annihilation emission path.

15 Claims, 8 Drawing Sheets

U.S. PATENT DOCUMENTS

| | | | |
|---|---|---|---|
| 2004/0158416 A1 | 8/2004 | Slates | |
| 2006/0002511 A1* | 1/2006 | Miller et al. | 378/65 |
| 2006/0113482 A1* | 6/2006 | Pelizzari et al. | 250/370.09 |
| 2006/0173294 A1 | 8/2006 | Ein-Gal | |
| 2006/0182326 A1* | 8/2006 | Schildkraut et al. | 382/132 |
| 2006/0193435 A1* | 8/2006 | Hara et al. | 378/65 |
| 2007/0003010 A1* | 1/2007 | Guertin et al. | 378/63 |
| 2007/0003123 A1* | 1/2007 | Fu et al. | 382/131 |
| 2007/0014391 A1* | 1/2007 | Mostafavi et al. | 378/63 |
| 2007/0043289 A1 | 2/2007 | Adair | |
| 2007/0055144 A1 | 3/2007 | Neustadter et al. | |
| 2007/0265528 A1 | 11/2007 | Xu et al. | |
| 2008/0031404 A1 | 2/2008 | Khamene et al. | |
| 2008/0130825 A1 | 6/2008 | Fu et al. | |
| 2008/0152085 A1 | 6/2008 | Saracen et al. | |
| 2008/0205588 A1 | 8/2008 | Kim | |
| 2008/0253516 A1 | 10/2008 | Hui et al. | |
| 2008/0273659 A1* | 11/2008 | Guertin et al. | 378/65 |
| 2008/0298536 A1 | 12/2008 | Ein-Gal | |
| 2009/0003655 A1 | 1/2009 | Wollenweber | |
| 2009/0086909 A1 | 4/2009 | Hui et al. | |
| 2009/0256078 A1 | 10/2009 | Mazin | |
| 2010/0067660 A1 | 3/2010 | Maurer, Jr. et al. | |
| 2011/0092814 A1 | 4/2011 | Yamaya et al. | |

OTHER PUBLICATIONS

Written Opinion mailed on May 4, 2009, for PCT Patent Application No. PCT/US2009/001500, filed on Mar. 9, 2009, 5 pages.

Written Opinion mailed on Jul. 20, 2012, for PCT Patent Application No. PCT/US2012/031704, filed on Mar. 30, 2012, 10 pages.

Chang, J.Y. et al. (2008). "Image-Guided Radiation Therapy for Non-Small Cell Lung Cancer," *J. Thorac. Oncol. FEB* 3(2):177-186.

Erdi, Y.E. (Feb. 2007). "The Use of PET for Radiotherapy," *Current Medical Imaging Reviews* 3(1):3-16.

International Search Report mailed on May 4, 2009, for PCT Patent Application No. PCT/US09/01500, filed on Mar. 9, 2009, 3 pages.

Yamaya, T. et al. (Jan. 14, 2008). "A Proposal of an Open PET Geometry," *Physics in Medicine and Biology* 53:757-773.

* cited by examiner

METHOD AND APPARATUS FOR EMISSION GUIDED RADIATION THERAPY

RELATED APPLICATIONS

This application is a continuation of U.S. patent application Ser. No. 12/367,679, filed Feb. 9, 2009, which claims the benefit under 35 U.S.C. 119(e) to U.S. Provisional Patent Application Ser. No. 61/036,709, filed Mar. 14, 2008, the contents of each of which are incorporated herein by reference in their entirety.

FIELD OF TECHNOLOGY

This disclosure relates to apparatus and method for radiation therapy and more particularly to apparatus and method for treating cancer tissue in the body using high energy radiation.

BACKGROUND

Radiation therapy (RT) is a method for treating cancerous tissue in the body using high energy radiation (e.g. x-rays) to kill tumor cells. There are two main types of RT: internal beam and external beam. Internal beam RT is achieved by implanting radioactive material within the patient inside or near the cancerous site to be treated. External beam RT is achieved by aiming a high energy beam of radiation through the patient so that it passes through the region to be treated. External RT has evolved significantly over the past few decades. In an effort to apply a lethal radiation dose to a tumor while sparing healthy tissue, techniques such as three-dimensional conformal beam RT are used to shape the beam to match the two-dimensional projection of the tumor onto the patient surface. Furthermore, the beam is applied at various angles around the patient and with varying intensities so as to maximize dose to the tumor while minimizing dose to the surrounding healthy tissue. This is known as intensity-modulated RT (IMRT).

However, uncertainty associated with tumor location and motion can limit effectiveness of external beam RT. Static errors arise from patient setup variability as well as natural changes in the tumor location due to shifting of the internal organs. These can change between treatments. Dynamic errors arise from tumor motion during treatment (e.g. due to patient breathing). Lung tumors, for example, are known to move on the order of 1-2 cm during normal patient respiration. This continuing problem has resulted in a new class of RT systems: image-guided RT (IGRT). These techniques involve imaging the tumor region using a conventional medical imaging modality (x-ray, CT, MRI, PET, etc.) both before and sometimes simultaneously during treatment so that the tumor location can be known at the time of treatment.

IGRT techniques, however, suffer either from a lack of specificity of the tumor imaging (e.g. in many cases it is nearly impossible to visualize the tumor boundaries from x-ray CT, or from poor temporal resolution (PET is the most sensitive modality to imaging cancer however it take minutes to form a good quality PET image). In either case, it is still very difficult to dynamically track a tumor during RT.

Positron emission tomography (PET) is a medical imaging modality that is frequently used to detect cancerous tissue in the body. A molecule labeled with a radioactive atom, known as a PET radiotracer, is first injected into the patient. The radioactive atoms inside the patient undergo radioactive decay and emit positrons. Once emitted from an atom, a positron will quickly collide with a nearby electron after which both will be annihilated. Two high energy photons (511 keV) are emitted from the point of annihilation and travel in opposite directions. When the two photons are simultaneously detected by two PET cameras, it is known that the annihilation occurred somewhere along the line joining the two PET cameras. This line is called a positron annihilation emission path. The information collected from thousands of these emission paths is used to gradually assemble an image of the PET radiotracer distribution in the body. The most commonly used PET radiotracer is fluorine-18 fluorodeoxyglucose (FDG). This is a glucose substitute and therefore is used to image the rate of metabolic activity in the body. Because cancerous tissue tends to be more metabolically active then healthy tissue, there is an increase in FDG uptake in a tumor relative to normal tissue and therefore an increase in the PET signal. FDG-PET is one of the most sensitive imaging modalities that can be used to detect the presence of cancer. It is used extensively for both diagnosis of cancer and monitoring of therapy. However, it is impractical to use PET simultaneously with external beam RT. PET imaging takes on the order of 10 minutes to acquire an image of reasonable quality which severely limits the use of PET as an agent for dynamic tracking of tumor position.

SUMMARY

The present subject matter relates to apparatus and method for scanning and aligning radiation along coincident positron annihilation emission paths. A method includes detecting a coincident positron annihilation emission path from a radioactive event intersecting a predetermined volume during a session, and aligning a radiation source along the emission path during the session. Various examples include repeated, timely alignment of radiation in response to individual detected emission events. Various examples include receiving location data to identify predetermined volumes and avoid directing radiation to radiation sensitive areas.

An apparatus is provided for aligning radiation during a radiation session. The apparatus comprising a radiation source, coincident positron emission detectors configured to detect coincident positron annihilation emissions originating within a coordinate system, and a controller in communication with the radiation source and the coincident positron emission detectors, the controller configured to identify coincident positron annihilation emission paths intersecting one or more volumes within the coordinate system and to align the radiation source along an identified coincident positron annihilation emission path.

This Summary is an overview of some of the teachings of the present application and is not intended to be an exclusive or exhaustive treatment of the present subject matter. Further details about the present subject matter are found in the detailed description and the appended claims. The scope of the present invention is defined by the appended claims and their legal equivalents.

DETAILED DESCRIPTION

The following detailed description of the present invention refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

The present subject matter relates to a new class of techniques termed emission guided radiation therapy ("EGRT"). One EGRT method includes using an emission modality that is highly sensitive to cancer directly during the treatment stage by responding to individual emission events using a beam of radiation along the detected path of emission. If the radiation response occurs within a sufficiently short time period after the emission detection, the tumor site will not have moved substantially and will be irradiated. Thus, tumor tracking is inherently achieved in emission guided radiation therapy and complete knowledge of the actual tumor location or motion is not required. By responding to a series of emission events from the tumor site with a series of respective radiation beams, treatment can be achieved effectively irrespective of tumor location uncertainty. It is also possible to treat more than one tumor simultaneously in this fashion. In addition, the same pre-planning procedure as is employed for current RT protocols may be carried out to identify a volume within which the tumor will always be present (including its motion) so that no radiation, or minimal radiation, is applied to regions where the tumor is not present, and/or so that treatment avoids radiation sensitive organs in the body.

Figure 1:
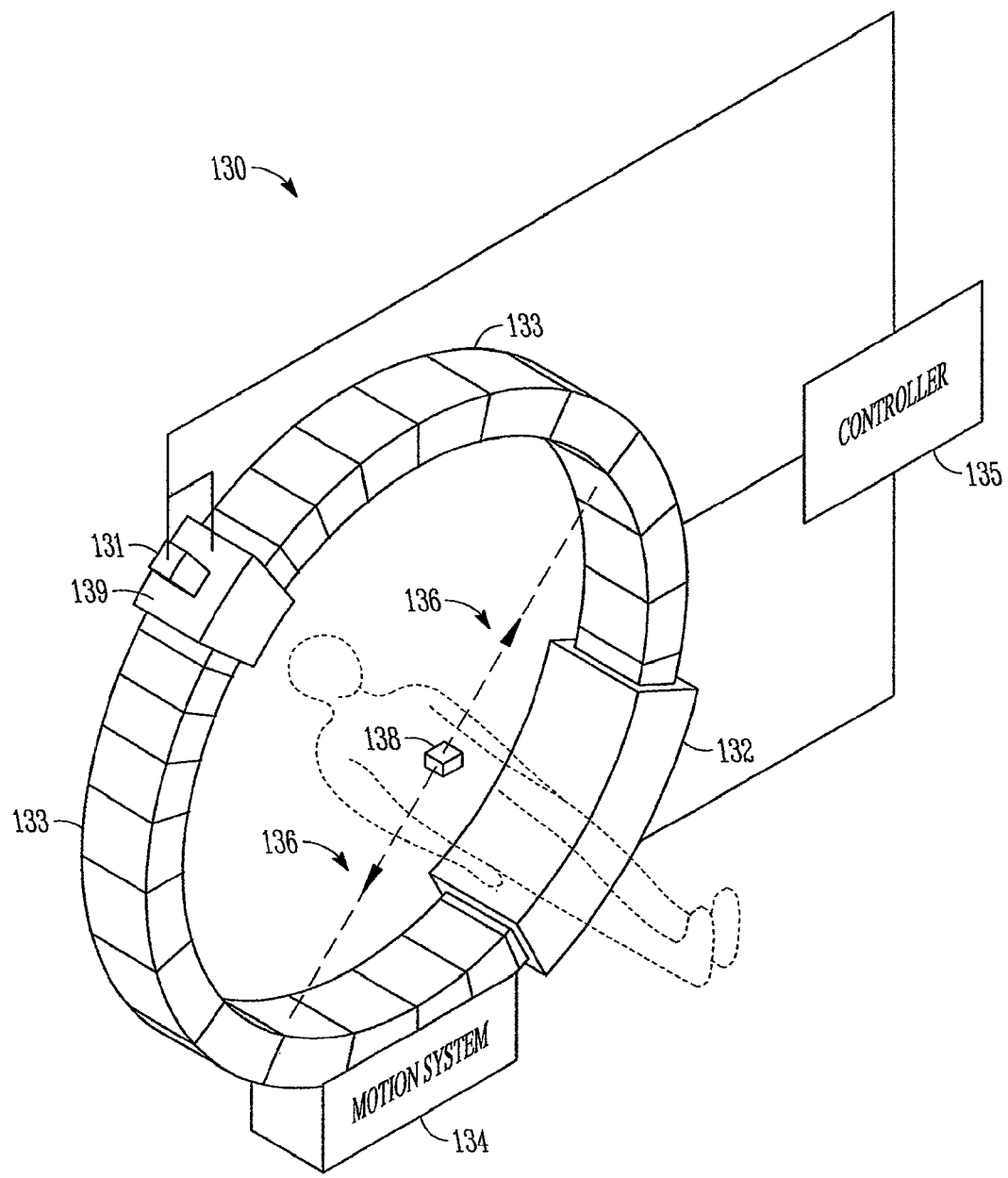
FIG. 1 shows an apparatus for aligning radiation along positron annihilation emission paths according to one embodiment of the present subject matter.

FIG. 1 shows an apparatus for sensing and aligning radiation along detected positron annihilation emission paths according to one embodiment of the present subject matter. In various embodiments, the apparatus 130 includes a circular moveable gantry supported by a frame (not shown), a radiation source 131, positron annihilation emission sensors 133, a motion system 134 and a controller 135. In various embodiments, the apparatus includes x-ray detectors 132 positioned opposite the radiation source to measure radiation applied to a volume of interest 138. The radiation source 131, x-ray detectors 132 and positron emission sensors 133 are mounted to the moveable gantry. The positron emission sensors 133 are mounted on the gantry between the radiation source 131 and the x-ray detectors 132. In various embodiments, the apparatus includes x-ray and positron emission sensors combined so that the positron emission detectors provide sensing capability around substantially the entire gantry circle from one side of the radiation source to the other. In one embodiment, the x-ray detectors include, but are not limited to, high energy, mega-electron Volt (MeV) detectors. The positron emission sensors 133 are adapted to detect positron annihilation events by sensing coincident photon paths 136 emitted during the events. In various embodiments, the motion system moves the gantry and attached equipment about the volume 138 to align the radiation source with the path of the detected emission. The controller 135 is connected to the radiation source 131, positron emission sensors 133, x-ray detectors 132 and the motion system 134. The controller 135 identifies coincident photon emission paths 136 intersecting an identified volume 138 and coordinates the alignment, configuration and triggering of the radiation source 131 to direct radiation to the volume 138 along the identified emission paths. In various embodiments, the controller receives location information for one or more volumes of interest 138 to limit any applied therapy to a region of interest. In various embodiments, the controller is programmed with one or more volumes that the system will not irradiate. Some examples of these volumes include radiation sensitive areas to protect from radiation, or perhaps an area which was treated previously and which needs to be untreated in any particular session. In some embodiments, volumes of interest 138 are identified in a first phase of a radiation session by detecting several positron annihilation emissions and mapping the activity. In various embodiments, the radiation source includes a collimation assembly 139 for shaping and precisely directing the radiation from the radiation source.

In various embodiments, the controller moves the radiation source, the positron emission detectors, or both the radiation source and the positron emission detectors using a common coordinate system. In one embodiment, the positron emission detectors are stationary and the radiation source is moveable using a robotic motion system referenced to a common coordinate system. In some embodiments, the radiation source and the positron emission detectors are both moveable and use separate motion systems referenced to a common coordinate system. It is understood that various motion systems are possible for moving the radiation source, the positron emission detectors or both the radiation source and the positron emission detectors without departing from the scope of the present subject matter including, circular gantries, rectilinear gantries, articulated arm robots, custom robotics or combinations thereof.

Figure 2:
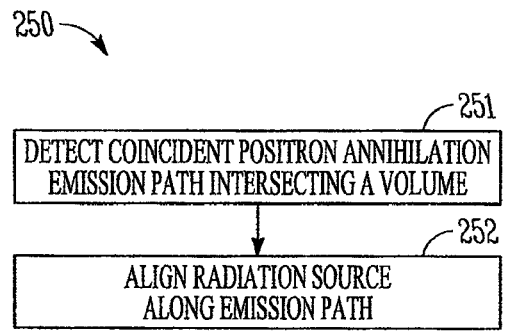
FIG. 2 is a flowchart for a method of aligning radiation along coincident positron annihilation emission paths according to one embodiment of the present subject matter.

FIG. 2 is a flowchart of a method 250 for scanning a volume during a radiation session according to one embodiment of the present subject matter. Often, a tumor is imaged a substantial period of time before undergoing radiation therapy. During therapy, radiation is directed to the location the tumor was at when last imaged. Tumors can migrate substantial distances in relatively short intervals of time. Such migrations can result from such innocuous events as a patient changing posture, coughing or even breathing. A typical goal of radiation therapy is to apply enough radiation to the tumor so as to kill the tumor tissue while also minimizing radiation applied to non-tumor tissue. If the tumor moves after it has been imaged, some radiation may miss the tumor during radiation, thus, some portions of the tumor may survive treatment and some healthy tissue may receive lethal amounts of radiation. Additionally, if during treatment, radiation is applied to portions of the tumor that are dead, the patient will be enduring more radiation than is necessary. In medical applications, the present method provides real-time tracking of live tumor tissue and direction of radiation to the tumor tissue. The method 250 includes detecting coincident positron annihilation emission paths from a radioactive event intersecting a volume 251 and aligning a radiation source along the emission path 252. In various embodiments, the method includes directing radiation along the detected emission path to the volume before the content of the volume moves substantially.

In medical applications, applying radiation along the detected positron annihilation emission path in a timely manner provides certainty that the radiation therapy is applied to living tumor tissue; even if the tumor has migrated since last imaged.

Figure 3:
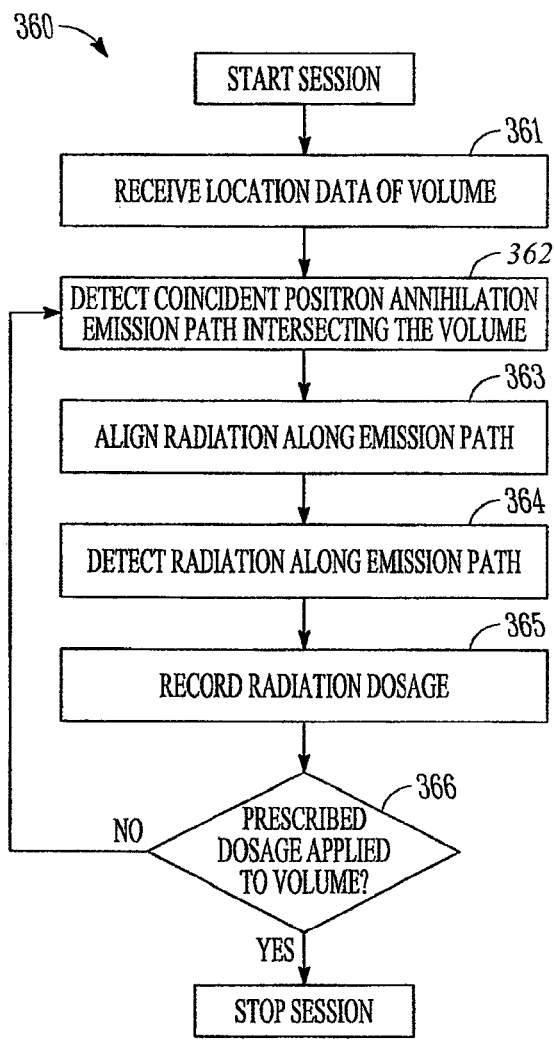
FIG. 3 is a flowchart for a method of aligning and directing a prescribed dose of radiation according to one embodiment of the present subject matter.

FIG. 3 is a flow chart of a method 360 for directing a predetermined dose of external radiation to a volume of interest during a radiation session according to one embodiment of the present subject matter. The method includes receiving location data describing one or more volumes of interest 361. In various situations, the data is generated during a pre-treatment planning stage. In some situations, substantial imaging has been done to diagnose and track a volume of interest such as an area of diseased tissue. This imaging can be used to establish probable volumes within which tumors of interest exist and move. The data may be generated from imaging completed during diagnosis. In some embodiments, location data of more than one volume is received such that radiation may be directed to several volumes during a session. Identifying volumes of interest, such as cancerous tumor tissue, for example, may include a number of modalities including, but not limited to, X-Ray imaging, Computed Tomography (CT), Magnetic Resonance Imaging (MRI), Positron Emission Tomography (PET) or combinations thereof. Other modalities are possible without departing from the scope of the present subject matter.

In various embodiments, prior to a radiation session, a volume of interest is provided with a radiotracer. The radiotracer provides a source of positrons for real-time tracking of the volume. The method then commences with receiving location data of the volumes 361, if not already received. In various embodiments, receiving the location data of the volume includes registering the volume with a reference point of the machine, such as the radiation source, for example. In various embodiments, registering the volume with the machine includes performing a low dose CT scan using the machine's radiation source. In some embodiments, receiving location data of one or more volumes and registering each volume with the machine includes detecting a number of emission events and mapping the events to identify the volumes. It is understood that other methods of registering a volume with the external radiation machine are possible without departing from the scope of the present subject matter. In some embodiments, receiving location data of the volumes includes receiving location data of areas not to irradiate.

The method further includes detecting coincident emission paths from a positron annihilation event intersecting a volume of interest 362, aligning the radiation source along the detected emission path 363 and then directing radiation along the detected emission path to the volume 364. In various embodiments, upon detection of an emission event, the downloaded location data are used to determine whether the event intersected a volume of interest.

In various embodiments, the radiation source and emission detectors move about the one or more volumes to allow for detection of emission events and direction of radiation from multiple angles. Directing radiation to a volume from multiple angles minimizes exposure of intervening material, such as healthy tissue, to radiation. In various embodiments, prior imaging is used to regulate intensity of the radiation source to account for the depth of the volume within other material. In various embodiments, as the session progresses, the controller analyzes and constructs a map of one or more volumes of interest from the emission events detected during the session. In various embodiments, as the map becomes more detailed, the controller selectively aligns and directs radiation along detected emission paths based on the map.

Upon directing radiation toward a volume, a controller records the amount or dose of radiation directed to the patient 365. In various embodiments, x-ray detectors located opposite the radiation source record the radiation directed toward and passing through the volume. The controller monitors the accumulated radiation and continues to detect emission events and direct radiation along detected emission paths until a prescribed dosage of radiation has been directed to each volume of interest 366. In various embodiments, accumulation of the detected positron emission events can be used to image the volume of interest and surrounding material. In medical applications, accumulation of the detected positron emission events can be used to construct an image of metabolic activity of the volume. In some embodiments, the image data may be used to modify subsequent treatment.

In various embodiments, such as those used in medical applications, volumes of interest, such as cancerous tumor tissue, are provided with a radiotracer as a source of positrons for real time tracking of the volume. A typical radiotracer includes unstable nuclides which emit positrons. The positron has the same mass as an orbital electron but is positively charged. A unique characteristic of the positron is that it can not exist at rest in nature. Once it loses its kinetic energy, the positron immediately combines with a negatively charged electron and undergoes an annihilation reaction in which the masses of the two particles are completely converted into energy in the form of two 0.511-MeV annihilation photons, which leave their production site at approximately 180 degrees from each other. The detection of the two 511-keV gamma rays forms the basis for targeting living tumor tissue with radiotracers.

A commonly used radiotracer in clinical practice and the study of cancers is fluorine-18 fluorodeoxyglucose (FDG), a metabolic PET radiotracer. FDG, a glucose analog, is taken up by high-glucose-using cells such as brain, kidney, and cancer cells, where phosphorylation prevents the glucose from being released intact. Thus, living diseased tissue will take up, and concentrate metabolic PET radiotracers more intensely than healthy tissue. Because dead tissue does not take up the radiotracer, an added benefit of a metabolic radiotracer is that it provides real-time tracking of the living tissue of the tumor. As a result, in applying the radiation therapy along detected emission paths, the method provides a high degree of certainty that the radiation is applied precisely to not only the tumor, but to the living tissue of the tumor. It is understood that the use of other radiotracers with positron-emitting radionuclide are possible without departing from the scope of the present subject matter including, but not limited to, Fluorine-18, Carbon-11, Oxygen-15, and Nitrogen-13.

FIGS. 4A-4D show a cross section of an apparatus 401 for detecting coincident positron annihilation emissions paths and aligning radiation to the emission paths according to one embodiment of the present subject matter. FIGS. 4A-4D includes a patient 420 positioned within the apparatus 401. The patient has living tumor tissue within a volume 422 to be irradiated. The apparatus includes a controller 407, a radiation source 402 to produce high energy radiation, a collimation assembly 410 to assist shaping and precisely directing the high energy radiation, an array of x-ray detectors 408, and an array of positron emission tomography (PET) sensors 404. The radiation source 402, collimation assembly 410, x-ray detectors 408 and PET sensors 404 are situated on a rotating gantry 406. The gantry 406 is mounted to a stationary frame (not shown). In various embodiments, a motion control system 409 connected to the controller 407 moves the gantry 406 and mounted equipment about the patient 420.

Figure 4A:
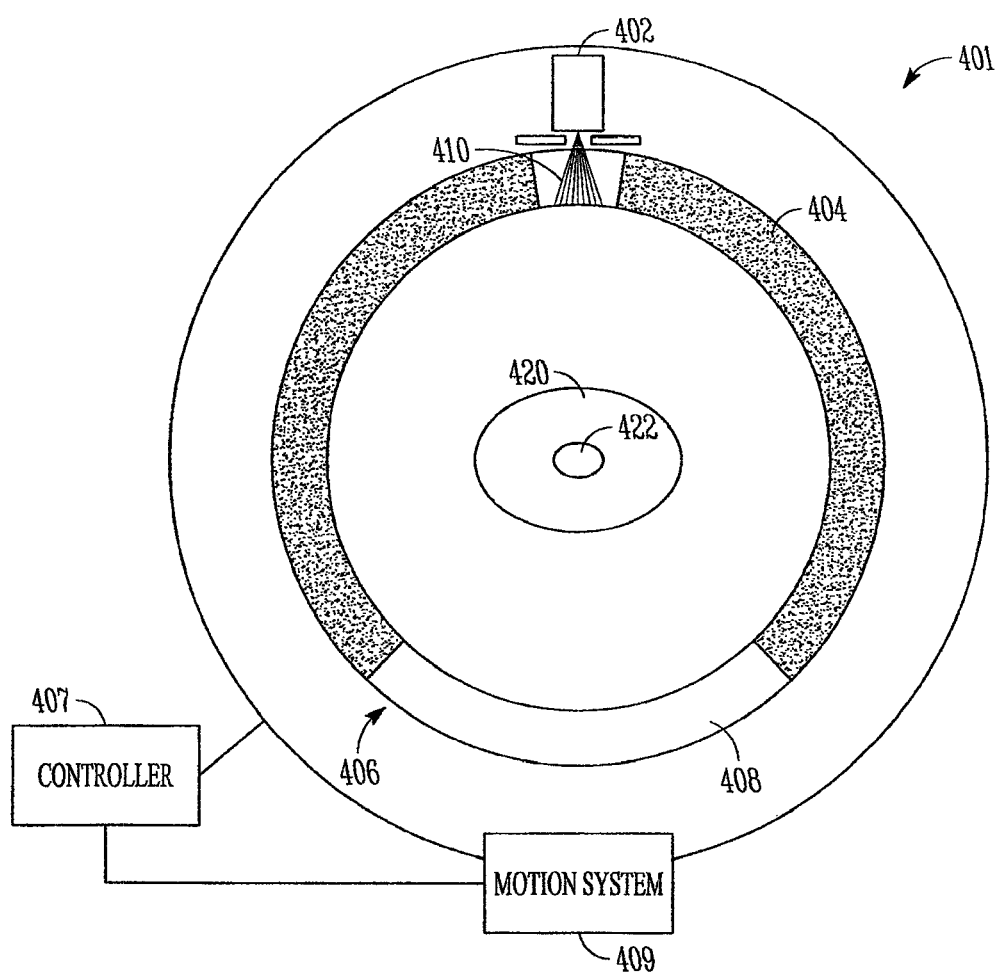
FIG. 4A-4D illustrates an apparatus for aligning radiation along positron annihilation emission paths according to one embodiment of the present subject matter.
Figure 4B:
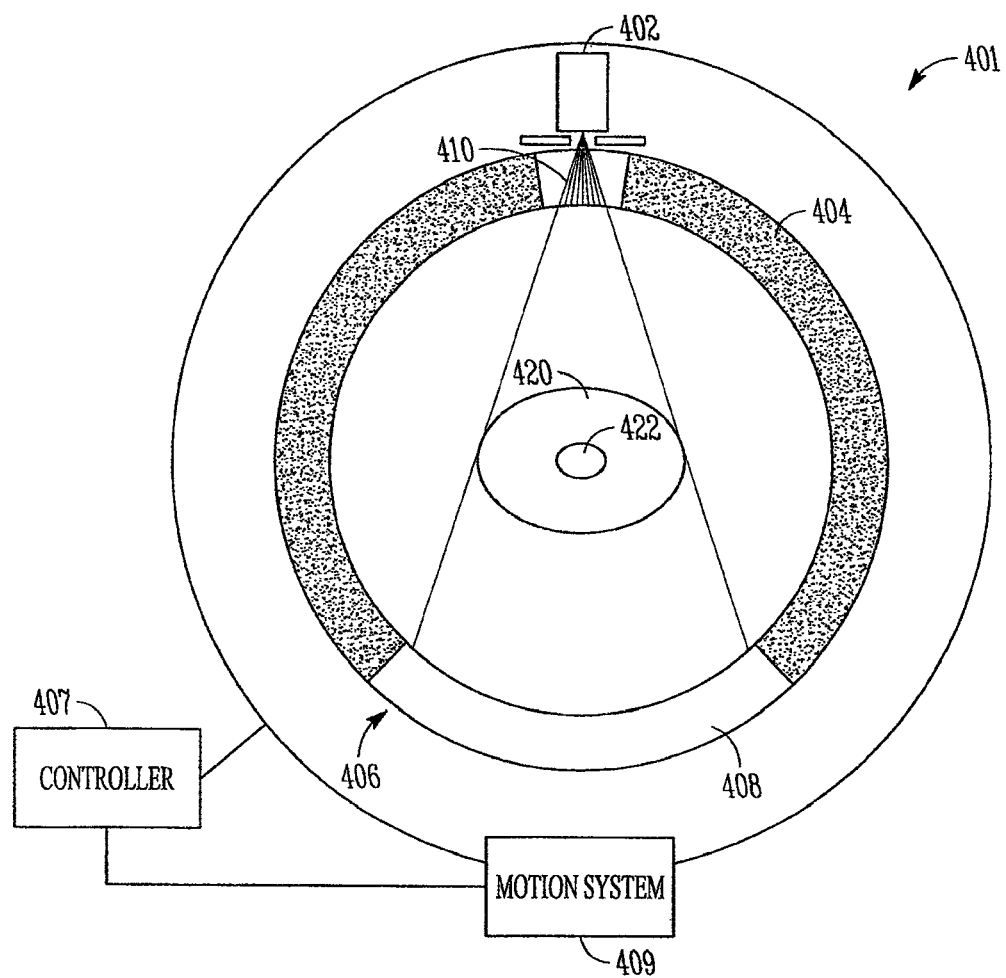

FIG. 4B shows the apparatus 401 performing a low dose, MeV CT scan to register the patient's position relative to the apparatus 401. Anatomic landmarks or other marking schemes may be used to register the patient's body position with the apparatus. Registration allows the controller to relate the geometric coordinates of the volume(s) of interest, including those volumes not to be irradiated, with the geometric coordinates of the apparatus 401. After registration, the controller 407 controls the apparatus 401 in monitoring positron annihilation emission paths intersecting the volume 422, aligning the radiation source to the emission paths and directing radiation along detected emission paths. While monitoring for positron annihilation events, the radiation source 402, collimation assembly 410, PET sensors 404 and high energy radiation detectors 408 rotate around the patient using the motion system 409 connected to the controller 407.

Figure 4C:
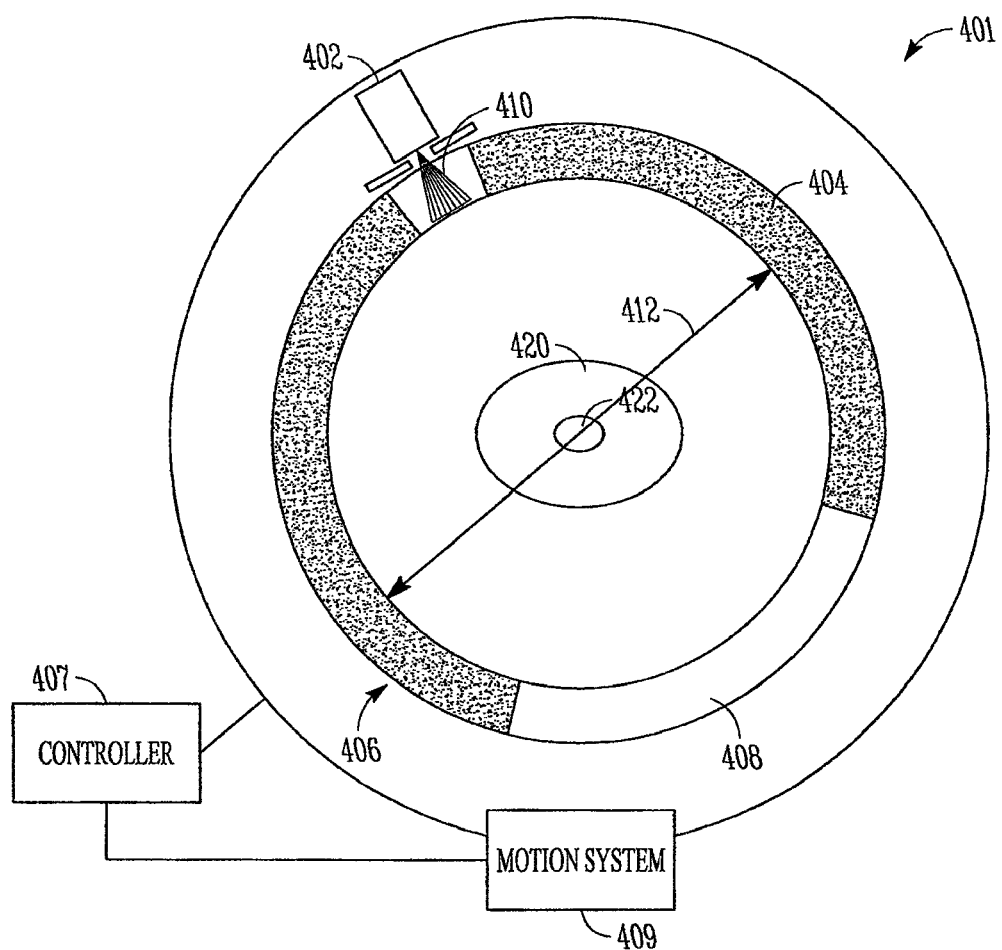

FIG. 4C shows detection of a coincident positron emission path 412 intersecting the volume 422. Upon detection of a coincident emission event and path 412, the controller 407, records the geometric coordinates of the coincident emission path. If the detected path 412 intersects a volume of interest 422, the controller 407 initiates alignment of the radiation source and triggers radiation along the path of the emission after the motion system has moved the radiation source 402 into alignment with the emission path 412. Applying the radiation along the same path as the emission provides a high degree of certainty that the radiation is applied precisely to living tissue of the tumor. In addition to moving the radiation source to the angle of a detected emission, alignment includes configuring the collimation assembly 410 to precisely direct the radiation along the positron emission path. In various embodiments, precise and timely alignment of the radiation includes reconfiguring the collimation assembly while the gantry 406 is rotating about the patient.

Figure 4D:
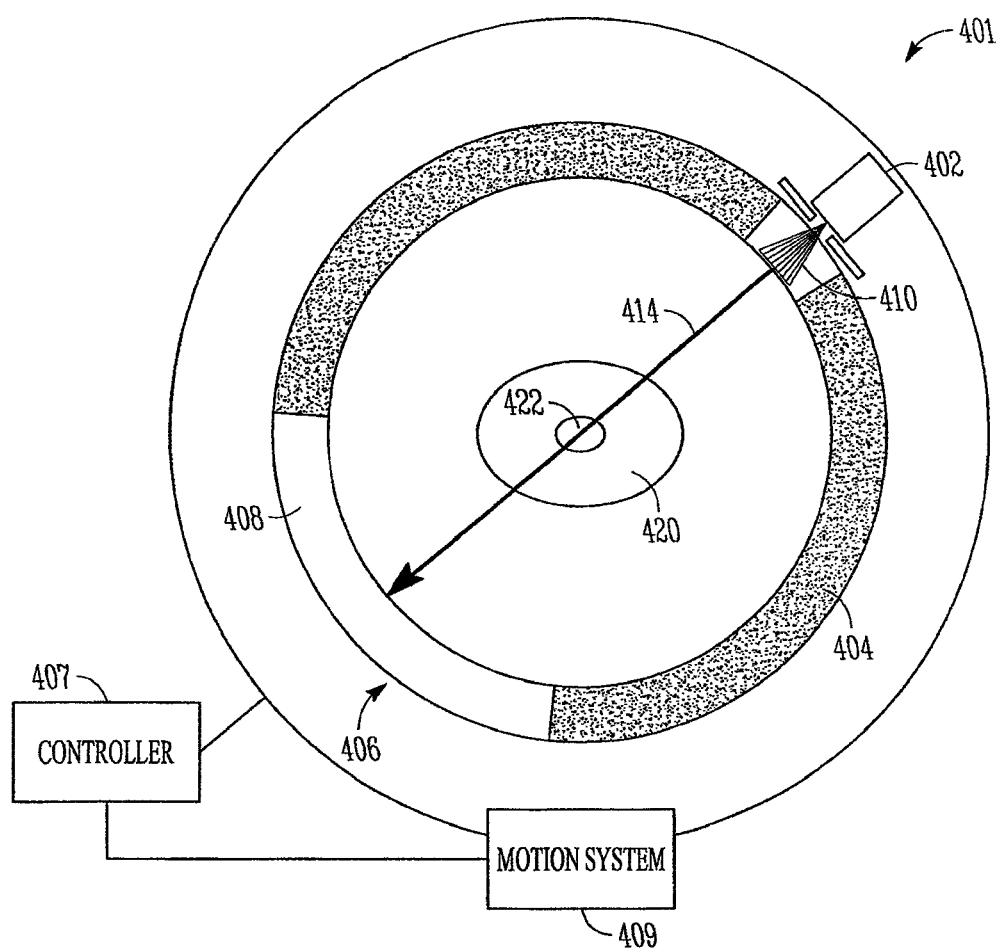

FIG. 4D shows the apparatus directing radiation along a detected emission path according to one embodiment of the present subject matter. The controller coordinates the motion of the gantry, configuration of the collimation assembly and triggering of the radiation source to provide radiation 414 from the radiation source 402 along the same path as detected positron emission paths. The collimation assembly 410 allows the radiation beam to be fragmented so that desired rays in the fan-beam may pass through while others are completely occluded. Reconfiguration of the collimation assembly occurs quickly so that a new configuration is possible for each angular position of the radiation source 402 around the gantry 406.

As the gantry 406 rotates, detection, alignment and triggering of radiation is repeated for multiple positron emission events until a desired radiation dose is achieved in each volume of interest. In various embodiments, the controller records readings received from the x-ray detectors 408 to verify the total radiation dosage. It is understood that x-ray detectors may be formed of one or more high energy detectors including, but not limited to, MeV detectors, high energy kilo-electron volt (keV) detectors or combinations thereof.

In various embodiments, the controller 407 includes data about the location of one or more tumors. In such embodiments, the controller coordinates detection of emission events and triggering and directing of radiation to the multiple volumes. In various embodiments, volume location data is downloaded into the controller from previous imaging. The data allows the controller to determine with a high degree of certainty whether a detected emission event path intersects with a volume of interest.

As discussed above, when positron emission events intersecting a volume of interest are detected, the controller 407 reconfigures the collimation assembly 410 to allow radiation from the radiation source 402 to follow the same path as the detected emission path within a specified time. In various embodiments, reconfiguration of the collimation assembly is accomplished on-the-fly as the gantry 406 rotates the radiation source 402 and sensors 404, 408 about the patient 420. Speed of the gantry rotation, processing delay of the controller, and location of the radiation source upon detection of an emission event are some factors that determine the delay between the emission event and directing and triggering radiation along the emission path. In medical applications, alignment of the radiation source to emission paths increases tracking accuracy of tumors even for motion of the tumors resulting from normal body functions such as breathing. In some embodiments, the gantry includes multiple radiation sources. Multiple radiation sources allow treatment to be completed more quickly, allow delay reduction between detection of an emission event and alignment of a radiation source or both quicker treatment and reduced delay.

In various embodiments, the apparatus aligns and directs radiation in response to individual positron annihilation events. In various embodiments, the controller queues detected positron annihilation emissions as the gantry rotates, aligns and directs radiation to previously detected emission paths. In some embodiments, the radiation source is aligned and directed sequentially along selected queued paths. In some embodiments, the radiation source is aligned and directed along selected queued paths depending on the present position of the radiation source about the volume, such that a more recently detected path may be selected because the radiation source will approach that path before an earlier detected path. In some embodiments, the controller queues selected emission paths for an interval of time and then aligns and directs radiation along selected paths of the queue before repeating the process by queuing additional emission paths. By adjusting the desired time interval between sensing an event and delivering radiation along the detected emission path, the apparatus can establish a queue of different numbers of radiation delivery paths. It can also use algorithms to provide the radiation with the least amount of movement of the apparatus. Other algorithms and procedures are possible without departing from the scope of the present subject matter.

In some embodiments, the controller paces alignment and triggering of the radiation source to cyclical functions of the patient such as breathing. For example, assume the breathing cycle of a patient has been sensed to repeat every few seconds. As the controller senses emission events intersecting a volume of interest, the controller records the phases of the breathing cycle in which these events occurred and controls a coordinated delay in moving, aligning and triggering the radiation source to coincide with the same phases of the breathing cycle.

Figure 5:
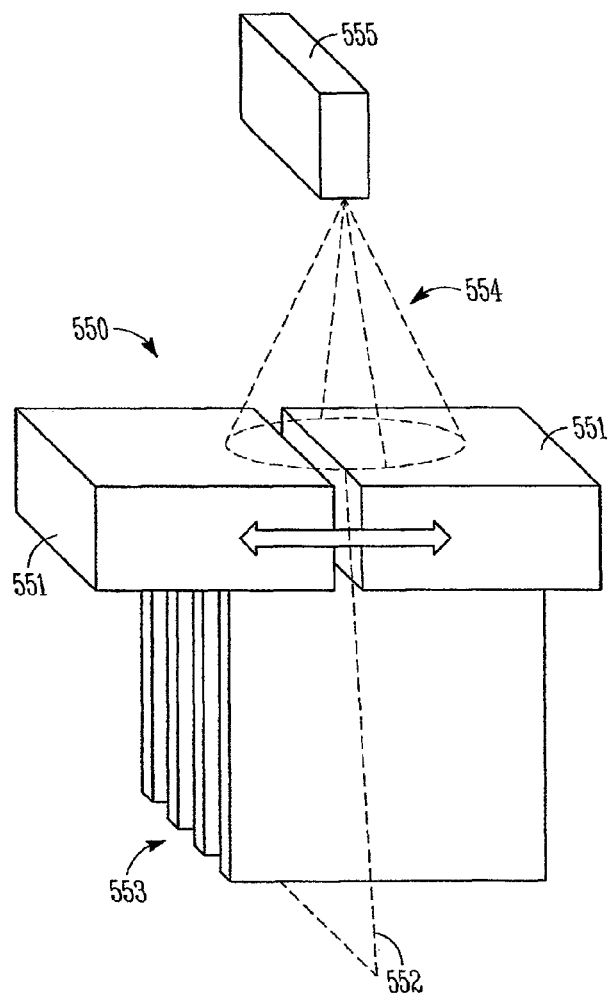
FIG. 5 shows a collimator assembly according to one embodiment of the present subject matter.

Various embodiments of the present subject matter align and direct radiation in a 2-D or a 3-D mode. In a 2-D mode, a multi-leaf radiation collimator is reconfigured for each specified angular position of the radiation source so that radiation paths lie within a fan whose vertex is at the source of radiation. FIG. 5 shows a collimator assembly 550 according to one embodiment of the present subject matter. A pair of collimator jaws 551 immediately preceding the multi-leaf collimator 553 restricts the conical divergence 554 of the radiation source 555 to a particular plane 552. Operation of the lower jaws 553 allows alignment of the radiation to multiple volumes within the plane of the radiation path. In various embodiments, a table may be translated in a continuous fashion or in a step-and-shoot fashion to treat multiple slices of a volume. If the table is translated continuously, the table speed should allow for a prescribed dose to each volume.

In the case of an apparatus employing a 3-D mode of treatment, the collimator jaws 551 restricting the conical radiation beam divergence 554 may be moved in coordination with the collimation assembly leaves 553. Although radiation is restricted to a particular plane, coordinated motion of the collimation assembly jaws allow various planes of treatment for a given position of the radiation source. For circular gantries and C-Arm apparatus, 3-D mode allows the collimation assembly to provide radiation at angles oblique to the central axis of the apparatus. Additionally, for a given position of the apparatus, the 3-D mode allows the controller to respond to multiple coincident emission paths within a larger portion of the field of view of a PET sensor array compared to 2-D mode.

Figure 6A:
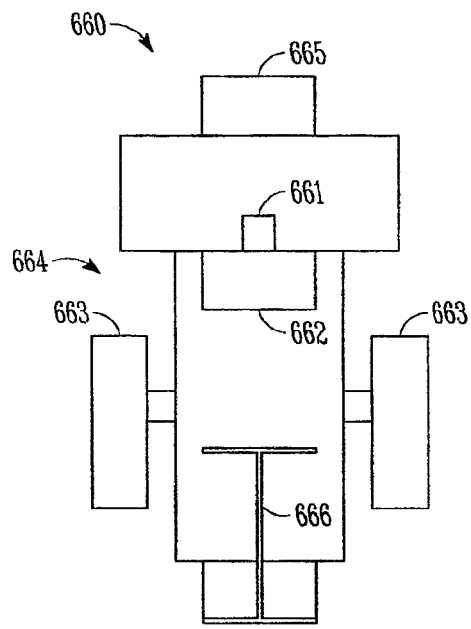
FIGS. 6A-6C shows a C-arm gantry for aligning radiation along positron annihilation emission paths according to one embodiment of the present subject matter.
Figure 6B:
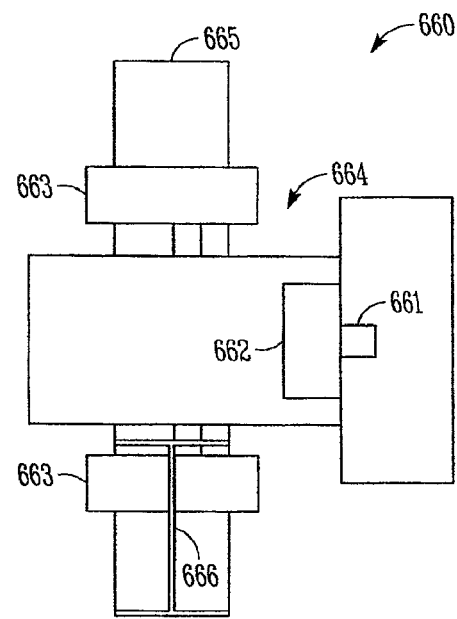
Figure 6C:
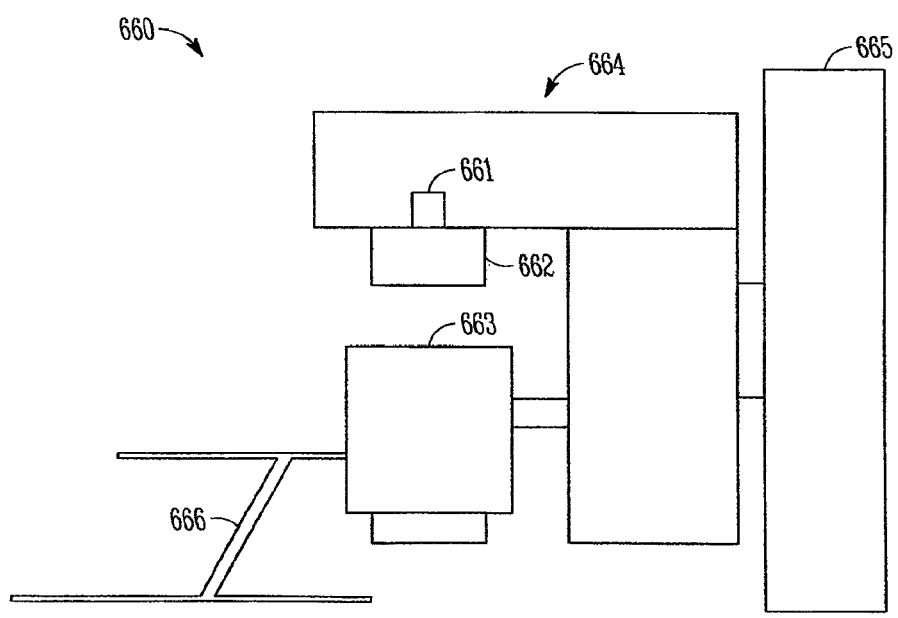

FIGS. 6A-6C shows a C-arm gantry apparatus 660 according to one embodiment of the present subject matter. The apparatus 660 includes a radiation source 661, collimation assembly 662 and PET cameras 663 mounted to a rotary section 664 of the apparatus. A fixed section 665 of the apparatus provides support for the rotary section 664. FIG. 6A shows a front view of the apparatus with the radiation source located above, a table 666 and the PET cameras 663 positioned at either side of the table 666. A controller (not shown) provides control and coordination of the radiation source 661, collimation assembly 662, PET cameras 663, and motion as the rotating section 664 moves the devices about the table 666. FIG. 6B shows a front view of the apparatus with the radiation source 661, collimation assembly 662 and PET cameras 663 rotated 90 degrees about the table 666. For 3-D mode treatment, a multi-leaf x-ray collimator is reconfigured for each specified angular position of the radiation source so that the radiation paths lie within a cone whose vertex is at the source of radiation.

In various embodiments, in order to treat multiple slices of a volume, the table 666 may by translated in a continuous fashion or in a step and shoot mode. FIG. 6C shows a side view of the C-arm gantry apparatus 660 with the table 666 translated toward the apparatus. In various embodiments, where the table is translated continuously, table speed is controlled to allow for a prescribed dose of radiation to be directed to each volume.

In various embodiments, the apparatus 660 includes high energy (MeV) detectors located opposite the radiation source to record and verify the amount, or dose, of radiation directed to each volume. In some embodiments, instead of MeV detectors, combined MeV/PET detectors are used. Combined MeV/PET detectors allow detection of both 511 keV PET emissions as well as high energy radiation. Such an arrangement increases the coverage of the PET detectors and allows for a faster radiation session. It is understood that other combinations of PET and high energy x-ray detectors are possible without departing from the scope of the present subject matter including but not limited to keV/PET detectors.

In various embodiments, the radiation includes x-rays produced by a linear accelerator (linac). Other radiation types and radiation sources are possible for providing radiation without departing from the scope of the present subject matter. Such radiation and radiation sources include, but are not limited to, high energy photons, radiation or particles produced by a radioactive isotope (e.g. iridium or cobalt60), high energy electrons, a proton beam, a neutron beam and a heavy ion beam.

In one embodiment, the apparatus is implemented using a single photon emission computed tomography (SPECT) setup with pinhole cameras and/or collimated SPECT sensors in place of the PET sensors to detect the direction of emitted photons from a radioactive event.

In one embodiment, the radiation source does not rotate. Radiation sources (e.g. lead encased cobalt60) are placed all around the gantry, alternating with the PET detectors. In this case, radiation from a particular radiation source would follow the emission path detected by an adjacent PET sensor pair.

In one embodiment, two or more radiation sources are affixed to the rotating gantry. The controller aligns each of the radiation sources to respond to distinct emission paths. Multiple radiation sources permit a smaller time window between detecting an emission path and directing radiation along that path, than if only a single radiation source is used.

In various embodiments, the apparatus provides other modes of radiation therapy for stand alone operation, or for simultaneous operation with emission guided radiation therapy. Other modes of radiation therapy include, but are not limited to, radiation treatment based on prior imaging of the treatment volumes, three-dimensional conformal beam RT, intensity-modulated RT or combinations thereof.

This application is intended to cover adaptations and variations of the present subject matter. It is to be understood that the above description is intended to be illustrative, and not restrictive. The scope of the present subject matter should be determined with reference to the appended claims, along with the full scope of legal equivalents to which the claims are entitled.

What is claimed is:

1. A method of treatment comprising:
   detecting an individual positron emission path originating from a volume of tissue using at least one positron emission detector mounted on a rotatable gantry, wherein the gantry further comprises at least one radiation source mounted thereon;
   rotating the gantry to position the at least one radiation source with respect to the individual detected positron emission path; and
   applying radiation to the volume of tissue before the tissue moves substantially.

2. The method of claim 1, wherein detecting the individual positron emission path, rotating the gantry, and applying radiation take place during a single treatment session.

3. The method of claim 1, wherein rotating the gantry positions the at least one radiation source at a first angle with respect to the individual positron emission path.

4. The method of claim 3, wherein rotating the gantry further comprises positioning the at least one radiation source at a second angle with respect to the individual positron emission path.

5. The method of claim 1, wherein the gantry is a circular gantry.

6. The method of claim 1, wherein the rotatable gantry further comprises an array of x-ray detectors mounted along the gantry.

7. The method of claim 6, wherein the array of x-ray detectors is positioned opposite the at least one radiation source.

8. The method of claim 6, wherein the rotatable gantry further comprises a collimation assembly configured to shape radiation from the at least one radiation source.

9. The method of claim 8, wherein rotating the gantry comprises configuring the collimation assembly with respect to the individual detected positron emission path.

10. The method of claim 1, further comprising:
    detecting an additional individual positron emission path originating from the volume of tissue;

rotating the gantry to position the at least one radiation source with respect to the additional individual detected positron emission path; and applying radiation to the volume of tissue.

11. The method of claim 1, further comprising:

detecting an additional individual positron emission path originating from a second volume of tissue;

rotating the gantry to position the at least one radiation source with respect to the additional individual detected positron emission path; and applying radiation to the second volume of tissue before the second volume of tissue moves substantially.

12. A method of treatment comprising:

detecting an individual positron emission path originating from a volume of tissue using at least one positron emission detector mounted on a first gantry;

rotating a second gantry comprising at least one radiation source mounted thereon to position the at least one radiation source with respect to the individual detected positron emission path; and applying radiation to the volume of tissue before the tissue moves substantially.

13. The method of claim 12, wherein detecting the individual positron emission path, rotating the second gantry, and applying radiation take place during a single treatment session.

14. The method of claim 13, further comprising rotating the first gantry.

15. A method of treatment comprising:

detecting an individual positron emission path originating from a volume of tissue using at least one positron emission detector mounted on a rotatable gantry, wherein the gantry further comprises at least one radiation source mounted thereon;

rotating the gantry to position the at least one radiation source with respect to the individual detected positron emission path; and applying radiation to the volume of tissue, wherein the radiation is applied without generating an image based on the individual detected positron emission path.

* * * * *